United States Patent [19]

Schwertner et al.

[11] 4,045,556
[45] Aug. 30, 1977

[54] DIPEPTIDE DERIVATIVES, PROCESS FOR MANUFACTURE AND PHARMACEUTICAL PREPARATIONS

[76] Inventors: Eberhard Schwertner, Heinrichsallee 55, 51 Aachen; Siegfried Herrling, Dohlenweg 33, 519 Stolberg, both of Germany

[21] Appl. No.: 622,804

[22] Filed: Oct. 16, 1975

[30] Foreign Application Priority Data

Oct. 16, 1974 Germany .............................. 2449167
June 21, 1975 Germany .............................. 2527723

[51] Int. Cl.$^2$ .................... A61K 37/00; C07C 103/52
[52] U.S. Cl. .......................... 424/177; 260/112.5 TR; 260/112.5 R
[58] Field of Search ............... 260/112.5 TR; 424/177

[56] References Cited

U.S. PATENT DOCUMENTS 3,912,705  10/1975  Fujino et al. ............... 260/112.5 TR

OTHER PUBLICATIONS

J. D. Roberts and M. C. Caserio, "Basic Principles of Organic Chemistry", Benjamin, Inc., New York, 1965, p. 664.

*Primary Examiner*—Delbert R. Phillips
*Attorney, Agent, or Firm*—Weiser, Stapler & Spivak

[57] ABSTRACT

Dipeptide compounds derived from histidyl-proline, namely acyl derivatives of histidyl prolinamide such as orotyl-L-histidyl-L-prolinamide, L-2-oxo-imidazolidine-4-carbonyl-L-histidyl-L-prolinamide, L-50-oxo-thiomorpholine-3-carbonyl-L-histidyl-L-prolinamide and others (and salts of such compounds with pharmaceutically acceptable acids) useful as psycho-stimulating or anti-depressive agents, respectively.

Also a process of preparation.

31 Claims, No Drawings

DIPEPTIDE DERIVATIVES, PROCESS FOR MANUFACTURE AND PHARMACEUTICAL PREPARATIONS

The dipeptide derivatives according to the invention are derived from histidyl-proline, one or both of the amino acids contained therein being optically active or racemic, preferably having the L-configuration.

The invention relates to compounds of formula I

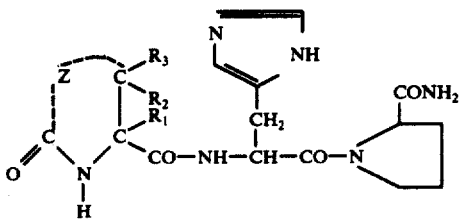

(I)

and salts of these compounds with pharmaceutically acceptable acids.

In formula I, the $R_1$ and $R_2$ may be equal or different and each represents hydrogen or an alkyl radical containing one to three carbon atoms. $R_1$ and $R_2$ together also can represent an additional bond between the carbon atoms to which said members are connected. $R_3$ represents a hydrogen atom or an alkyl radical containing one to three carbon atoms. Z represents a divalent structure which completes the ring to a five or six membered ring, said divalent structure being a member of the group consisting of the structures

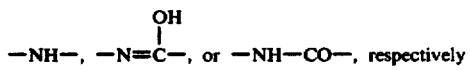

or —NH—CO—, respectively

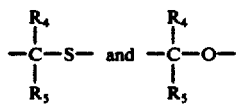

wherein $R_4$ and $R_5$ are equal or different and each represent hydrogen or an alkyl radical containing one to three carbon atoms.

The dipeptide derivatives of formula I are acyl derivatives of histidyl proline amide derived from a carboxylic acid of formula II

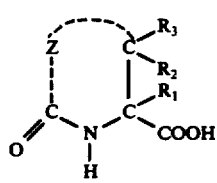

(II)

Preferred acids of formula II in the present invention are orotic acid, imidazolidine-(2)-one-(4)-carboxylic acid and thiomorpholine-(5)-one-(3)-carboxylic acid.

Other suitable acids of formula II are, for instance, morpholine-(5)-one-(3)-carboxylic acid, thiomorpholine-(5)-one-(2,2)-dimethyl-(3)-carboxylic acid, (4)-carboxy-imidazole-(2)-one, thiomorpholine-(6)-methyl-(5)-one-(3)-carboxylic acid, 5-methyl-, 5-ethyl- or 5-propyl-orotic acid and others.

In case $R_1$ and $R_2$ do not form a second bond between the carbon atoms to which said members are connected and/or where $R_4$ and $R_5$ are different also the acyl groups derived from the acid of formula II can be present in the compounds of formula I in racemic or optically active form, preferably in the L-configuration.

Especially preferred members of the compounds of formula I are orotyl-histidyl-prolinamide and salts thereof, wherein most preferably both amino acids are present in the L-configuration.

Due to the basicity of the histidyl radical the compounds of formula I can form salts with acids. Further objects of the present invention accordingly are the salts of the compounds of formula I with (in form of salts) pharmaceutically acceptable inorganic or organic acids, such as hydrochloric acid, hydrobromic acid, sulfuric acid, phosphoric acid, formic acid, acetic acid, propionic acid, benzoic acid, salicylic acid, phenyl acetic acid, benzenesulfonic acid and others.

Surprisingly, the compounds of formula I (and their salts) possess biological properties, which are equivalent or superior to those of pyroglutamyl-histidyl-proline amide, which compound normally is designated as "thyrotropin releasing hormone" or "TRH". The effects of the new compounds are considerably longer lasting than those of the known product. Of special value in therapy is that the relation of the central stimulating effects to the endocrinological effects is shifted in favor of the new compounds, when compared with the effects of the known TRH, favorably to the pharmacologically valuable properties.

The compounds of formula I may be administered orally or parenterally. Their effects are observed quickly. For instance, on parenteral administration the effects occur already after ten minutes.

The most remarkable effects of the new products indicated in pharmacological tests is a central stimulation action. On administering equal doses of TRH and orotyl-L-histidyl-L-proline amide, respectively, to test animals the new compound has a stimulating effect on the central nervous system about five times stronger and several times longer than TRH.

The toxicity of the compounds of formula I is very low. Due to these valuable properties the new compounds can be used as therapeutics, for instance, as psycho-stimulating agents or anti-depressive agents, respectively. The compounds are of therapeutic value in animals and humans.

Suitable pharmaceutical preparations containing the compounds of formula I or their salts are for oral use tablets, dragees, granules, capsules, drops, syrups, for intranasal application or administration via bronchial sprays and for parenteral application sterile aqueous solutions.

A further object of the invention is the manufacture of the compounds of formula I.

Conveniently, the compounds of formula I are prepared by reacting histidyl proline amide (having the desired optical configuration) with an acid of formula II in presence of an agent, which is able to split off water, especially in presence of a carbodiimide, preferably dicyclohexyl carbodiimide or with a functional derivative of an acid of formula II as, for instance, an acid halide, anhydride, mixed anhydride, azide or an activated ester.

Instead of the acid of formula II or the functional derivative thereof, also a compound of formula IIa

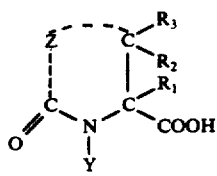

(IIa)

wherein $R_1$, $R_2$, $R_3$ and Z have the same meaning as above and Y represents a group cleavable by hydrogenolysis, preferably a carbobenzoxy group or a substituted carbobenzoxy group, or, a functional derivative of the acid of formula IIa, as, for instance, an acid halide, anhydride, mixed anhydride, azide of an activated ester may be used and splitting off the group Y by means of hydrogenolysis with catalytically activated hydrogen, as is known in prior art.

During the reaction of histidyl proline amide with the acid of formula II or IIa, respectively, or a derivative thereof, the 1-(3)-position of the imidazole group of the histidyl residue may be protected against acylation. Suitable protective groups are known from peptide synthesis to those skilled in the art. Such groups are, for instance, the carbobenzoxy group, substituted carbobenzoxy groups, the trityl, o-nitrophenoxy acetyl or the tert. butyloxycarbonyl group and other groups known per se, which after the reaction is completed can be split off by hydrolysis or hydrogenolysis.

Instead of the histidyl proline amide with free or protected imidazole group in the invention also a derivative thereof, obtained by reacting it in a manner known, per se, with a silylating agent, derived from a trialkylsilanol or a dialkyl-silanediol (each alkyl radical thereof containing one to three carbon atoms) as, for instance, hexamethyldisilazane, trimethylchlorosilane, trimethylsilylacetamide, dimethyldichlorosilane and others, may be used. After the acylation reaction (which in this case is performed in absence of a protone activity solvent) is finished the silyl groups can easily be split off by hydrolysis or alcoholysis.

In preparing the compounds of formula I it is possible also to react proline amide with a compound of formula III

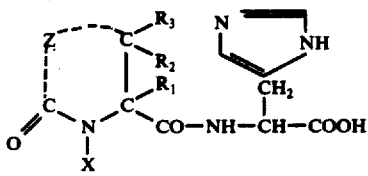

(III)

wherein $R_1$, $R_2$, $R_3$ and Z have the same meaning as above and X represents a hydrogen atom or a member of the group Y as defined before, or a derivative of the compound of formula III in the which the 1-(3)-position of the imidazole group is protected reversibly as described above in the presence of an agent which is able to split off water, especially in presence of a carbodiimide, preferably dicyclohexyl carbodiimide or with a functional derivative of a compound of formula III as, for instance, an acid halide, anhydride, mixed anhydride or an activated ester and split off the protecting group from the imidazole group, if present, and the member X, if other than hydrogen.

Furthermore, compounds of formula I can be prepared by reacting a compound of formula IV

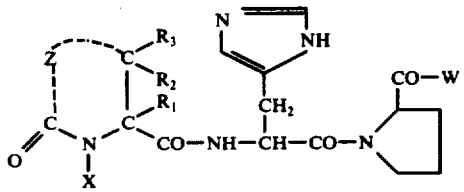

(IV)

wherein $R_1$, $R_2$, $R_3$, X and Z have the same meaning as above and W represents a hydroxy, acyloxy, p-nitrophenoxy, tri- or pentachlorophenoxy-, pentafluorophenoxy, pyridyloxy, phenylmercapto, p-nitrophenylmercapto or cyanomethyloxy group or the residue of N-hydroxysuccinimide, with ammonia or a compound generating ammonia under the reaction conditions (as, for instance, ammonium carbonate). In this reaction also a derivative of the compound of formula IV may be used wherein the 1-(3)-position of the imidazole group is protected reversibly in the manner described herein above.

Orotyl histidyl proline amide (one or both of the amino acid groups contained therein being optically active or racemic, but preferably having the L-configuration) can preferably be manufactured by reacting histidyl proline amide (having the desired optical configuration) with an acid of the formula

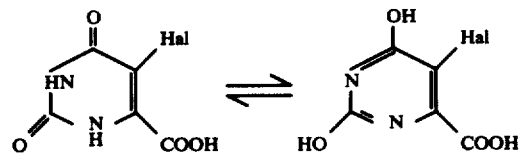

(V)

wherein Hal represents a chlorine or a bromine atom in presence of an agent able to split off water, especially in presence of a carbodiimide, preferably dicyclohexylcarbodiimide or with a functional derivative of such an acid of formula V, as, for instance, an acid halide, anhydride, mixed anhydride, azide or an activated ester and thereafter dehalogenating the intermediate by hydrogenolysis.

During the reaction of histidyl proline amide with the acid of formula V or the derivative thereof, the 1-(3)-position of the imidazole group of the histidyl residue may be protected against acylation. Suitable protective groups are those mentioned already herein above. In this last described method to perform the invention, especially such protective groups may be used which can be split off by hydrogenolysis (as, for instance, the carbobenzoxy group, substituted carbobenzoxy groups or the o-nitrophenoxyacetyl group). In this case the removal of the protective group from the intermediate occurs concurrently with the hydrogenolysis of the halogen atom. Naturally, it is also possible, however, to protect the imidazole group with groups which can be split off by hydrolysis (as, for instance trityl or tert. butyloxycarbonyl groups and others) and to remove such protective groups from the intermediate product or from the product obtained by hydrogenolysis of the halogen atom from the intermediate.

The hydrogenolysis of the halogen atom is done by means of catalytically activated hydrogen. Preferably a noble metal hydrogenation catalyst as, for instance, palladium or platinum on charcoal, on barium sulfate, on alumina, on calcium or barium carbonate and other noble metal catalysts known, per se, are used in the hydrogenolysis, which can be performed under normal or increased pressure, preferably at room temperature. Solvents like water or mixtures of water with lower alcohols (methanol, ethanol) or with tetrahydrofuran, dioxane and the like are preferably used in the hydrogenolysis step. It is, however, also possible to use glacial acetic acid and the like.

The hydrogen halide formed during the hydrogenolysis is preferably bound as soon as it occurs. To that end the hydrogenolysis is performed in presence of an agent able to bind hydrogen halides. If the above-mentioned preferred or other non-acidic solvents are used, suitable hydrogen halide binding agents are, for instance, magnesium oxide, barium oxide, alkali hydroxides, ammonia or ammonium hydroxide, respectively, triethylamine or salts of such bases with acids which are remarkably weaker than hydrogen halide being formed as, for instance, alkali carbonates or acetates. Suitable media for the performance of the hydrogenolysis step are also, for instance, solutions of alkali, earth alkali, ammonium or amine acetates in acetic acid.

Mixed anhydrides of the acids of formulae II, IIa, III and V are preferably derived from trimethyl acetic acid or from mono esters of carbonic acid, especially those in which the carbonic acid is esterified with aliphatic alcohols containing one to four carbon atoms. Suitable activated esters of said acids are those with p-nitrophenol, tri- or pentachlorophenol, pentaflurorophenol, N-hydroxysuccinimide, 2- or 4-hydroxypyridine, thiophenol, p-nitrothiophenol, hydroxyacetonitrile, 1-hydroxybenzotriazole and other hydroxy- or mercapto compounds conventionally used in peptide chemistry to prepare activated esters from acids.

The compounds of formula I and their salts are relatively stable products. They can, therefore, be purified, for instance, by dissolving and reprecipitation, by recrystallization but also by column chromatography or countercurrent distribution.

The following non-limiting examples further illustrate the invention. All temperature references are uncorrected. No importance was attached to obtain maximum yields in carrying out the tests on which the example are based. One skilled in the art can by adjusting the conditions obtain improved yields, if desired.

EXAMPLE 1 a. 79.2 g of N-benzyloxycarbonyl-L-2-oxo-imidazolidine-4-carboxylic acid (prepared as described by T. Shiba et al, Bull. Chem. Soc. Japan, Vol. 41, 2748-53 (1968)) and 38.1 g of N-hydroxysuccinimide are dissolved in 200 ml of dimethylformamide. After chilling to 0° C a solution of 61.8 g of N,N'-dicyclohexylcarbodiimide in 100 ml of dimethylformamide is added and the mixture is stirred for one hour at 0° C and thereafter for 12 hours, during which time the mixture is allowed to warm to room temperature. The dicyclohexylurea formed is filtered off and the filtrate is evaporated to a small volume. 600 ml of hot iso-propanol are added and after chilling to room temperature the crystals are filtered off. The crude product thus obtained (melting point 178° - 181° C) is used in the next step without purification.

b. 40.5 g of L-histidine and 21.9 g of sodium hydrogen carbonate are dissolved in 1000 ml of water and the solution of 92.2 g of the product obtained in step (a) in 1000 ml of dioxane is added thereto at room temperature. The mixture is stirred for 24 hours and then evaporated under reduced pressure. The residue is redissolved in 300 ml of water, the pH-value adjusted to 7 and thereafter the mixture is stored at 0° C until the crystallization of the N-benzyloxycarbonyl-L-2-oxoimidazolidine-4-carbonyl-L-histidine is completed. The material is filtered off by suction and recrystallized from 1.7 liters of boiling water.

Yield: 66.9 g = 64% of the theoretical; Melting point: 180° - 182° C; $[\alpha]_D^{23} = -18.9°$ (c=1 in dimethylformamide).

c. 60.2 g of the material obtained in step (b), 21.6 g of 1-hydroxy-benzotriazole and 22.5 g of L-prolinamide hydrochloride are suspended in 200 ml of dimethylformamide and then chilled to −10° C. While stirring 16.5 ml of N-methylmorpholine and thereafter a solution of 30.9 g of dicyclohexylcarbodiimide in 50 ml of dimethylformamide is added. The mixture is stirred for 24 hours during which time it is allowed slowly to warm to room temperature. The precipitate formed is sucked off and the filtrate is evaporated under reduced pressure. The residue is treated with 100 ml of water for 12 hours at 0° C. After filtration the solution is evaporated under reduced pressure and the residue thus obtained subjected to countercurrent distribution in the system n-butanol/water. The fractions containing the main product are combined and evaporated under reduced pressure.

A further purification is possible by chromatograpy on silica gel (0.2 – 0.5 mm). For instance, 3.5 g of the product may be dissolved in water and poured on a column containing 180 g of silica gel. On eluting with water first removal of the impurities occurs which is controlled by measuring the ultraviolet absorption spectrum of the eluate at 254 nm ($=2.54\text{cm}^{-5}$). Thereafter the main product is eluted by treatment with water/dioxane (2:1). The combined fractions containing the main product are evaporated under reduced pressure and the residue is dried over phosphorus pentoxide. Thus, 19.9 g of N-benzyloxycarbonyl-L-2-oxoimidazolidine-4-carbonyl-L- histidyl-L-prolinamide (27% of the theoretical yield) are obtained.

Melting point: 169° - 173° C; $[\alpha]_D^{25} = -87.7°$ (c = 0.36 in methanol).

Instead of the N-methylmorpholine in step 1(c) also 20.9 ml of triethylamine may be used.

The material obtained after the isolation by countercurrent distribution may also be further purified by column chromatography on basic aluminium oxide using methanol/chloroform (3:1) as solvent.

d. 19.9 g of the product of step (c) are dissolved in a mixture of 100 ml each of water and tetrahydrofuran and then treated with hydrogen for 5 hours in presence of palladium black obtained from 4 g of palladium-II-chloride. After the hydrogenolysis is complete the catalyst is removed and the filtrate treated with activated charcoal, filtered and the clear solution thus obtained is evaporated to a small volume under reduced pressure. The remaining aqueous solution is lyophylized to give 12.8 g (=89% of the theoretical yield) of L-2-oxo-imidazolidine-4-carbonyl-L-histidyl-L-prolinamide hydrate, melting at 172° - 173° C.

$[\alpha]_D^{23} = -52.4°$ (c = 1 in methanol);

$C_{15}H_{21}N_7O_4 \cdot 2H_2O$ (399.4). Calculated: C,45.10%; H,6.32%; N,24.55%; Found: C,45.73%; H,6.44%; N,24.76%.

EXAMPLE 2

15.6 g of orotic acid, 14.4 g 1-hydroxybenzotriazole and L-histidyl-L-prolinamide dihydrobromide (obtained from 38.5 g N-benzyloxycarbonyl-L-histidyl-L-prolinamide (K. Inouye et al., Bull. Chem. Soc., Japan 44, 1689–91 (1971) by removal of the benzyloxycarbonyl group by means of a 40% solution of hydrogen bromide in glacial acetic acid) are mixed with 200 ml of dimethylformamide. After chilling to −5° C, 27.8 ml of triethylamine are added while stirring and thereafter the solution of 20.6 mg of N,N'-dicyclohexylcarbodiimide in 50 ml of dimethylformamide is admixed. The reaction mixture is stirred for 24 hours during which time it is allowed to warm to room temperature. The precipitate formed is separated and the filtrate is evaporated under reduced pressure. The residue is treated with 200 ml of water for 12 hours at 0° C. After filtration the filtrate is stirred at room temperature for 10 minutes with 170 g of a cationic exchanger in free acidic state as, for instance, the product known under the trade name "Dowex-50 WX 4 (200 to 400 mesh)". The cationic exchanger carrying the product is separated by filtration and washed thoroughly with water, methanol and again with water. Thereafter the resin is stirred for five minutes with about 200 ml of 1n ammonia, filtered and washed several times with 1n ammonia. The combined filtrates are evaporated under reduced pressure to a volume of about 100 ml, treated with activated charcoal and then lyophilized. The product is two times heated to boiling with 250 ml each of absolute ethanol.

Further purification can be performed by column chromatography of a solution of this material in water/methanol (1:2) on basic aluminium oxide. The same solvent mixture is used for elution, which is controlled by measuring the ultraviolet absorption spectrum at 254 nm (= 2.54 cm$^{-5}$). First, the impurities (together with small amounts of the main product) are eluted followed by the pure main product. The combined fractions containing the main product are evaporated under reduced pressure. The residue is dissolved in a small volume of water and lyophylized to give 11.25 g (28% of the theoretical yield) of orotyl-L-histidyl-L-prolinamide hydrate.

Melting point: 250° C.; $[\alpha]_D^{22} = -45.8°$ (c = 1 in methanol)

$C_{16}H_{19}N_7O_5 \cdot H_2O$ (407.4); Calculated: C,47.20%; H,5.19%; N,24.12%; Found: C,47.95%; H,5.27%; N,24.10%.

The same product may also be obtained by reacting L-histidyl-L-prolinamide with orotyl chloride (J.med.-Chem. 6, 334–335 (1963) which acid chloride preferably is freed of unreacted orotic acid by dissolving in absolute tetrahydrofuran.

EXAMPLE 3

4.8 g of 5-chloro orotic acid, 3.6 g of 1-hydroxybenzotriazole and L-histidyl-L-prolinamide dihydrobromide (prepared from 9.7 g N-benzyloxycarbonyl-L-histidyl-L-prolinamide as described in Example 2) are mixed with 150 ml of dimethylformamide. After chilling to −5° C while stirring 7.0 ml of triethylamine and then the solution of 5.2 g of N,N'-dicyclohexylcarbodiimide in 20 ml of dimethylformamide are added. Under continuous stirring the mixture is stored for 90 minutes at −5° to 0° C and thereafter for 24 hours, during which time it is allowed to warm to room temperature. The precipitate formed is separated by filtration and the filtrate is evaporated under reduced pressure at a temperature of about 35° C. The residue is treated with 75 ml of water, stored for 12 hours at 0° C and filtered. The filtrate is stirred for 10 minutes with 75 g of a cationic exchanger in the free acid form (as, for instance, the product named in Example 2). After separating the resin it is washed four times with 250 ml of water each and four times with 50 ml of methanol each. Then the cationic exchanger resin is suspended in 100 ml of water, while stirring treated with 120 ml of 1n ammonia, sucked off and washed six times with 20 ml of 1n ammonia each. The combined ammoniacal filtrates are, at about 35° C under reduced pressure, evaporated to a small volume and finally lyophylized. The residue is two times recrystallized from water/ethanol (1:1) and thereafter dried in vacuum over phosphorus pentoxide. Thus, 4.7 g (44.8% of the theoretical yield) of 5-chloroorotyl-L-histidyl-L-prolinamide, melting at 204° – 206° C are obtained.

$[\alpha]_D^{23} = -36.2°$ (c = 1.16 in methanol)

Calculated: C,45.25%; H,4.27%; N,23.12%; Cl,8.37%; Found: C,44.99%; H,5.05%; N,22.64%; Cl,8.31%.

The same product is obtained by reacting L-histidyl-L-prolinamide with 5-chloro orotyl chloride (prepared by treating 5-chloro orotic acid in benzene in the presence of dimethylformamide with thionylchloride).

EXAMPLE 4

To 15 ml of water are added 165 mg of anhydrous sodium acetate and 100 mg of 5% palladium on charcoal. On a shaking apparatus the mixture is treated with hydrogen until the absorption stops. Then a solution of 850 mg of 5-chloro orotyl-L-histidyl-L-prolinamide in 30 ml of water is added and shaking in a hydrogen atmosphere is continued at normal pressure and room temperature until 2m moles (about 50 ml) of hydrogen or consumed. The catalyst is filtered off, the filtrate is extracted two times with ether and then the aqueous layer is evaporated at room temperature under reduced pressure to a volume of about 2 to 3 ml and diluted with two times it volume of methanol. This solution is poured on a column of 150 g of basic aluminium oxide, followed by elution with methanol/water (2:1), controlled by measuring the ultraviolet absorption spectrum at 254 nm. The fractions containing the main product are combined, evaporated under reduced pressure and finally lyophylized. Thus 780 mg (96% of the theoretical yield) of orotyl-L-histidyl-L-prolinamide hydrate (i.e., the same product as prepared in Example 2) are obtained.

EXAMPLE 5

The procedure is the same as described in Example 4, but there are used, however, instead of the sodium acetate 100 mg of magnesium oxide and the extraction with ether is omitted.

EXAMPLE 6

100 mg of 5% palladium on charcoal in 15 ml of glacial acetic acid are pretreated with hydrogen. Then a solution of 850 mg of 5-chloro-orotyl-L-histidyl-L-prolinamide in 30 ml of glacial acetic acid are added and the mixture is shaken in a hydrogen atmosphere at normal pressure and at room temperature. After consumption of 2 m moles of hydrogen the catalyst is filtered off, the filtrate evaporated to a small volume and treated with absolute ether. The precipitate is separated, washed with ether and dried to give orotyl-L-histidyl-L-prolinamide-hydrochloride in almost quantitative yield.

EXAMPLE 7

5-bromo-orotic acid is used in the procedure described in Example 3 to give 5-bromo orotyl-L-histidyl-L-prolinamide which is hydrogenolysed as described in Example 5. Thus, the orotyl-L-histidyl-L-prolinamide-hydrate (i.e., the product of Examples 2, 4 and 5) is obtained in a yield of 39% of the theoretical yield (calculated on the amount of 5-bromo orotic acid used).

EXAMPLE 8

To 150 ml of dimethylformamide are added 9.7 g of L-5-oxo-thiomorpholine-3-carboxylic acid (Tetrahedron 28, 4503-13 (1972)) and L-histidyl-L-prolinamide dihydrobromide (prepared from 23.2 g of N-benzyloxycarbonyl-L-histidyl-L-prolinamide as described in Example 2). After chilling to $-10°$ C while stirring 16.7 ml of triethylamine and then a solution of 12.3 g of N,N'-dicyclohexyl-carbodiimide in 50 ml of dimethylformamide are added. The mixture is stirred for 24 hours during which time the temperature is allowed to rise to room temperature. Thereafter, the precipitate formed is filtered off, the filtrate is evaporated under reduced pressure and the residue thus obtained is mixed with 200 ml of water. After storing for two hours at room temperature it is filtered and the filtrate is treated with a cationic exchanger resin and thereafter with 1n ammonia in the manner described in Example 2. The combined ammoniacal filtrates are evaporated under reduced pressure at temperatures below 35° C. The residue is subjected to countercurrent distribution in the system n-butanol water. The fractions containing the main product are combined and evaporated under reduced pressure. The residue is dissolved in water, treated with activated charcoal and lyophylized. 6.9 g (30% of the theoretical yield) of L-5-oxo-thiomorpholine-3-carbonyl-L-histidyl-L-prolinamide hydrate, melting at 155° – 157° C, are obtained.

$[\alpha]_D^{23} = -48.5°$ (c = 0.52 in methanol).

EXAMPLE 9

To 100 ml of dimethylformamide are added 5.1 g of 2-oxo-imidazole-4-carboxylic acid, 5.8 g of 1-hydroxybenzotriazole and L-histidyl-L-prolinamide dihydrobromide (prepared as described in Example 2 from 15.4 g of N-benzyl-oxycarbonyl-L-histidyl-L-prolinamide). After chilling to $-5°$ C while stirring 11.1 ml of triethylamine and thereafter the solution of 8.3 g of N,N'-dicyclohexylcarbodiimide in 30 ml of dimethylformamide are added. The stirred mixture is chilled for 30 minutes longer and then it is stored for 12 hours at room temperature. The precipitate formed is sucked off and the solution is evaporated under reduced pressure and at a temperature of about 35° C. The residue is mixed with 100 ml of water, stored for 12 hours at 0° C, filtered and then the filtrate is treated with a cationic exchanger and thereafter with 1n ammonia as described in Example 2. The ammoniacal filtrates are combined, evaporated under reduced pressure to a small volume and finally lyophylized. The residue is subjected to countercurrent distribution in the system n-butanol/water. The fractions containing the main product are combined, evaporated to dryness and the residue is dissolved in 50 ml of methanol and reprecipitated by addition of 500 ml of chloroform, which treatment then is repeated once. After drying in vacuum 4.7 g (27% of the theoretical yield) of 2-oxo-imidazole-4-carbonyl-L-histidyl-L-prolinamide trihydrate are obtained. This substance on heating above 180° C begins to sinter and on heating to 212° C it is molten.

$[\alpha]_D^{23} = -45,3°$ (c = 0.64 in methanol);
$C_{15}H_{19}N_7O_4 \cdot 3H_2O$ (415.4); Calculated: C,43.35%; H,6.07%; N,23.60%; Found: C,43.66%; H,5.35%; N,23.59%.

EXAMPLE 10 a. To a solution of 12.0 g L-cystine in 300 ml of liquid ammonia such amount of sodium (about 5 g) is added in small pieces, that the deep blue color remains for about 25 – 30 seconds, thus indicating a small excess of sodium, which thereafter is removed by addition of a few crystals of ammonium chloride (until the mixture is colorless). Now 10.8 g of 2-chloro-propionamide are added while stirring and after 10 minutes the ammonia is evaporated. The residue is dissolved in about 150 ml of water and the pH value of the solution is adjusted to 7 by addition of hydrochloric acid. After filtration the filtrate is evaporated under reduced pressure and the dry residue is suspended in 200 ml of glacial acetic acid, heated to boiling for 10 minutes, whereafter the glacial acetic acid is distilled off under reduced pressure. The residue is extracted three times with 200 ml of hot methanol each. The combined extracts are evaported, the remaining material is dissolved in 50 to 100 ml of water and then the pH value of the solution is adjusted to about 2. Crystals begin immediately to deposit which after storing at 0° C are isolated by filtration and recrystallized two times from about 50 ml of water. The product is dried over phosphorous pentoxide. Thus, 6.6 g (38% of the theoretical yield) of 5-oxo-6-(D,L) methylthiomorpholine-3(L)-carboxylic acid is obtained. The product is pure enough to be used in the following step.

For analysis the material is recrystallized twice from ethanol and twice from a mixture of ethanol/water (1:1).

Melting point: 186 – 188° C; $[\alpha]_D^{23} = +37.7°$ (c = 1 in methanol).

$C_6H_9NO_3S$ (175.2) Calculated: C,41.35; H,5.17; N,7.98; S,18.30; Found: C,41.03; H,5.09; N,8.06; S,18.01.

b. 17.5 g of 5-oxo-6-(D,L)-methyl-thiomorpholine-3(L)-carboxylic acid, 14.4 g of 1-hydroxybenzotriazole and L-histidyl-L-prolinamide dihydrobromide (prepared as described in Example 2 from 38.5 g of N-benzyl-oxycarbonyl-L-histidyl-L-prolinamide) are dissolved in 200 ml of dimethylformamide. The mixture is stirred and after cooling to $-5°$ C 27.8 ml of triethylamine and then a solution of 20.6 g of N,N'-dicyclohexylcarbodiimide in 30 ml of dimethylformamide are added. Under continuous stirring the mixture is stored for 1 hour at $-5$ to 0° C and thereafter for 12 hours at room temperature, after which time the precipitate formed is filtered off. The filtrate is evaporated under reduced pressure at about 35° C. The residue is mixed with 150 ml of water, stored for 12 hours at 0° C, filtered and then the filtrate is treated with a cationic exchanger resin and thereafter with 1n ammonia as described in Example 2. The residue obtained by evaporating the ammoniacal filtrate under reduced pressure to dryness is recrystallized twice from water, once from ethanol/water (1:1) and then three times from n-butanol, saturated with water. After drying over phosphorous pentoxide 5-oxo-6(D,L)-methyl- thiomorpholine -3(L)-carbonyl-L-histidyl-L-prolinamide trihydrate is obtained.

The combined mother liquors from the recrystallizations are evaporated and the residue is again recrystallized to give additional amounts of the product. The total yield is 14.5 g = 31.4% of the theoretical.

Melting point: 140°- 142° C; $[\alpha]_D^{25} = -33.5°$ (c = 1 in methanol).

$C_{17}H_{24}N_6O_4S \cdot 3H_2O$ (462.5); Calculated: C,44.15%; H,6.55%; N,18.17%; S,6.93%; Found: C,44,69%; H,6.47%; N,18.52%; S,6.54%.

EXAMPLE 11 a. 7.5 g of D-(-)-penicillamine, 2.9 g of sodium and 5.2 g of chloroacetaminde are reacted in 500 ml of liquid ammonia in the manner described in Example 10(a). The reaction product is dried over phosphorous pentoxide and then boiled for 15 minutes with 140 ml of glacial acetic acid. The residue obtained after evaporation of the glacial acetic acid is dissolved in 60 ml of water. The pH value of this solution is adjusted to about 2 by addition of hydrochloric acid and then the mixture is stored at 0° C. The crystals formed are sucked off and recrystallized from 60 ml of water. Thus, 7.0 g (74% of the theoretical yield) of D-5-oxo-2,2-dimethyl-thiomorpholine-3-carboxylic acid are obtained.

Melting point 189° - 192° C; $[\alpha]_D^{23} = -14.2°$ (c = 1 in methanol). $C_7H_{11}NO_3S$ (189,239); Calculated: C,44.35% H,5.82%; N,7.41%; S,16.93%; Found: C,44.82%; H,5.41%; N,7.92%; S,17.14%.

b. 13.2 g of D-5-oxo-2,2-dimethyl-thiomorpholine-3-carboxylic acid, 10.1 g of 1-hydroxybenzotriazole, L-histidyl-L-prolinamide dihydrobromide (obtained from 38.5 g of N-benzyloxycarbonyl-L-histidyl-L-prolinamide as described in Example 2) 27.8 ml of triethylamine and 14.4 g of N,N'-dicyclohexylcarbodiimide are reacted and worked up in the manner described in Example 10(b). In the present case, however, the material obtained after evaporating the ammoniacal filtrate of the cationic exchanger under reduced pressure to dryness is subjected to counter-current distribution in the system n-butanol/water. The fractions containing the main product are combined and evaporated under reduced pressure. Portions of 2 g of the residue are dissolved in methanol/water (1:1) and chromatographed on a column of 350 g of basic aluminium oxide. The elution is controlled by measuring the ultraviolet absorption spectrum at 254 nm and the fractions containing the main product are combined and evaporated under reduced pressure. For final purification the residue is subjected again to counter-current distribution in the system toluene/methanol/chloroform-/water (3:4,8:1,2).

The fractions containing the pure product are combined, evaporated to dryness under reduced pressure, the residue being redissolved in water and lyophylized.

Thus, 7.6 g (24.8% of the theoretical yield calculated on the used amount of the product of Example 11(a)) of D-5-oxo-2,2-dimethyl-thiomorpholine-3-carbonyl-L-histidyl-L-prolinamide hydrate, melting at 153° - 155° C are obtained. $[\alpha]_D^{24} = -83°$ (c = 1 in methanol)

$18H_{26}N_6O_4S \cdot H_2O$ (440.536); Calculated: C,49.07%; H,6.41%; N,19.08%; S,7.28%; Found: C,48.80%; H,6.43%; N,19.08%; S,724%.

EXAMPLE 12

To 100 ml of dimethylformamide are added, while stirring at room temperature, 17.0 g of 5-methyl orotic acid, 14.4 g of 1-hydroxybenzotriazole and 27.8 ml of triethylamine. After 10 minutes the mixture is chilled in an ice bath and 10 minutes later a solution of 20.6 g of N,N'-dicyclohexyl-carbodiimide in 30 ml of dimethylformamide and then L-histidyl-L-prolinamide dihydrobromide (obtained as described in Example 2 from 38.5 g of N-benzyloxycarbonyl-L-histidyl-L-prolinamide) and a further amount of 100 ml of dimethylformamide are added. The mixture is stirred for 30 minutes in the ice bath and then for 12 hours at room temperature and thereafter worked up as described in Example 2 until and including the preliminary purification with a cationic exchanger. The residue of the ammoniacal solution is recrystallized from 110 ml of ethanol. After chilling for 24 hours to 0° C the product is filtrated by suction and dried over phosphorous pentoxide. 2 g portions of this material are dissolved in methanol/water (1:1) and chromatographed over a column of 350 g basic aluminium oxide. The elution is controlled by measuring the ultraviolet absorption spectrum at 254 nm and the fractions containing the pure main product are combined and evaporated under reduced pressure. The residue is dissolved in methanol, filtered, evaporated to dryness, redissolved in water and lyophylized. Thus, 14.4 g (30.4% of the theoretical yield) of 5-methyl-orotyl-L-histidyl-L-prolinamide trihydrate melting at 222° - 227° C with decomposition are obtained.

$[\alpha]_D^{24} = -46.8°$ (c = 1 in methanol)

$C_{17}H_{21}N_7O_5 \cdot 3H_2O$ (457.459); Calculated: C,44.68%; H,5.95%; N,21.43%; Found: C,44.67%; H,5.98%; N,21.79%.

Further amounts of the product may be obtained by combining and evaporating to dryness the mother liquors and the fractions obtained in the chromatography containing impure main product and column chromatography of the residue in the manner described above.

EXAMPLE 13

The procedure is the same as described in Example 12, there are used, however, 18.4 g of 5-ethyl orotic acid instead of the methyl orotic acid and after the preliminary purification with a cationic exchanger the further purification is here made as follows:

The dry residue of the ammoniacal solution is subjected to counter-current distribution in the system n-butanol/water. The fractions containing the main product are evaporated under reduced pressure, the residue obtained is redissolved in water and lyophylized. Finally, it is recrystallized twice from water. Thus, 12.3 g (28.3% of the theoretical yield of 5-ethyl-orotyl-L-histidyl-L-prolinamide hydrate are obtained.

Melting point 186° C. $[\alpha]_D^{24} = -46.0°$ (c = 0.5 in methanol)

$C_{18}H_{23}N_7O_5 \cdot H_2O$ (435,427); Calculated: C,49.64%; H,5.79%; N,22.52%; Found: C,49.50% H,5.87%; N,22.59%.

The mother liquors are lyophylized and portions of 2 g of the residue are dissolved in methanol/water (1:1) and chromatographed on a column of 350 g of basic aluminium oxide. The elution is controlled by measuring the ultraviolet absorption spectrum at 254 nm. The fractions containing the desired product are evaporated under reduced pressure. The residue obtained is dissolved in methanol, filtered, evaporated to dryness, redissolved in water and lyophylized to give a further amount of 4.1 g (9.4% of the theoretical yield) of the desired product. Thus the total yield is 16.4 g = 37.7% of the theoretical yield.

EXAMPLE 14

The procedure is the same as described in Example 12. There are used, however, 19.8 g of 5-n-propyl-orotic acid instead of the methyl orotic acid, and after the preliminary purification with a cationic exchanger the final purification is performed as follows.

The dry residue of the ammoniacal solution is dissolved in 90 ml of ethanol by heating. The solution is stored for 12 hours at 0° C, then mixed with 100 ml of ice-cold ethanol and filtered by suction. The solid material thus obtained is recrystallized first from methanol/ethanol (1:5) and then from methanol/water (1:1) to give pure 5-n-propylorotyl-L-histidyl-L-prolinamide hydrate.

The combined mother liquors are evaporated to dryness and the residue thus obtained is recrystallized from methanol/water (1:1), methanol/ethanol (1:5) and again from methanol/water (1:1). Thus further amounts of the desired product are obtained. The total yield is 17.1 g = 38.0% of the theoretical.

Melting point: 187° C; $[\alpha]_D^{24} = -48.6°$ (c = 0.5 in methanol).

$C_{19}H_{25}N_7O_5 \cdot H_2O$ (449,493); Calculated: C,50.77%; H,6.06%; N,21.82%; Found: C,50.86%; H,6.12%; N,22.19%.

Following the procedures described above, especially those explained in the examples, the following compounds of Formula I are prepared (In cases where no particulars of the configuration are given any of the three components of the compounds of Formula I, i.e., the prolinamide, the histidine and the acid of Formula II is present in the racemic state, in the L-or in the D-configuration. As stated already hereinabove, the L-configuration is preferred.):

Orotyl-D,L-histidyl-D,L-prolinamide;
Orotyl-L-histidyl-D-prolinamide;
Orotyl-L-histidyl-D,L-prolinamide;
L-2-oxo-imidazolidine-4-carbonyl-L-histidyl-DL-prolinamide;
5-isisopropylorotyl-histidyl-prolinamide;
2-oxo-5,5-dimethyl-imidazolidine-4-carbonyl-histidyl-prolinamide;
2-oxo-4,5-dimethyl-imidazolidine-4-carbonyl-histidyl-prolinamide;
2-oxo-5-ethyl-imidazolidine-4-carbonyl-histidyl-prolinamide;
2-oxo-5-methyl-5-ethyl-imidazolidine-4-carbonyl-histidyl-prolinamide
5-oxo-2,2,6-trimethyl-thiomorpholine-3-carbonyl-histidyl-prolinamide;
5-oxo-2,3,6-trimethyl-thiomorpholine-3-carbonyl-histidyl-prolinamide;
5-oxo-6,6-dimethyl-thiomorpholine-3-carbonyl-histidyl-prolinamide;
5-oxomorpholine-3-carbonyl-histidyl-prolinamide; and
5-oxo-2,6-dimethylmorpholine-3-carbonyl-histidyl-prolinamide.

The compounds of the invention have useful biological and pharmacological properties.

The endocrinological properties of typical compounds of the invention, such as L-2-oxo-imidazolidine-4-carbonyl-L-histidyl-L-prolinamide-dihydrate (Compound A) and of orotyl-L-histidyl-L-prolinamide-dihydrate (Compound B) are compared to that of TRH, the thyrotropin-releasing hormone. It has been shown in standard tests that in comparison with TRH, Compounds A and B were required in a ten-times greater dose than TRH to obtain an equally marked thyrotropin release.

The compounds of the invention have been found to be effective psycho-stimulants and are thus useful as anti-depressives in the therapy of psychiatric disorders.

A series of standard tests were run. The compounds of the invention, as typified by Compounds A and B are marketly more effective than TRH in counteracting the lowering of body temperature caused by reserpine when tested as described below.

Mice are intraperitoneally injected with 8 mg of reserpine per kilogram of body weight with a solution of reserpine, in 5% of ascorbic acid. After twenty-four hours the temperature of the animal has considerably dropped to a temperature, hereinafter designated as the "initial temperature", which is the reference temperature against which the effect of the compounds is measured. Then the test substance is injectd intraperitoneally. Thereafter, every twenty minutes, the temperature (rectal) is recorded over three hours. The sum of the differences between the measured values and the initial temperature are noted. These are reported below for different dosages.

Table I

| BODY TEMPERATURE TEST | | | | |
|---|---|---|---|---|
| | Dosage mg/kg | | | |
| Substance | 2 | 5 | 10 | 20 |
| TRH | 18.4 | 16.5 | 27.9 | 32.8 |
| A | 20.8 | 26.1 | 32.8 | 40.1 |
| B | 34.6 | 42.3 | 55.3 | 67.1 |

From the above data it is evident that Compounds A and B are considerably more effective than TRH is this standard test in counteracting the temperature lowering effect of reserpine.

Compounds A, B and L-5-oxo-thiomorpholine-3-carbonyl-L-histidyl-L-prolinamide-hydrate (Compound C) were also found to stimulate the mobility of animals in the following test.

Test mice were injected ten to twenty hours before the experiment with 5 mg of reserpine per kilogram of body weight, intraperitoneally. The animals developed until the beginning of the experiment a marked hypomobility. The test substances (TRH, A, B and C) are then injected intraperitoneally to groups of ten mice. Another group of ten mice pretreated with reserpine only acted as control group. The movement and activity of the animals are determined, measured and registered, the animals being confined in a photocell activity cage.

Table II

| TEST OF MOTILITY | | | |
|---|---|---|---|
| | Dosage mg/kg | | |
| Substance | 3 | 5 | 10 |
| TRH | 0.9 | 1.2 | 44.0 |
| A | 17.0 | 21.7 | 94.1 |
| B | 98.0 | 106.0 | 104.0 |
| C | 51.0 | 72.0 | 69.0 |

The average motility measurement for the reserpine pretreated control animals is 14.2, the untreated mice is 123. The data in the Table shows the effectiveness of the compounds tested in counter-acting the activity lowering effect of reserpine.

It is known that the toxicity of amphetamine is increased by administration of anti-depressive compounds, especially those that have a central nervous system stimulating activity, this activity being evidenced by an increased mortality in the test. This effect is reported in the Table below.

The test substances were intraperitoneally injected and fifteen minutes later the test animals were administered amphetamine in a dose of 7 mg per kilogram. The Table shows the number of dead mice (in percent) after sixty minutes after treatment with the amphetamine. Those animals which were treated only with amphetamine, as control, were still all alive at that time.

Table III

| | MORTALITY RATE | | | | |
|---|---|---|---|---|---|
| | Dosage mg/Kg | | | | |
| Substance | 10 | 20 | 50 | 100 | 200 |
| TRH | 20% | 25% | 55% | 65% | 65% |
| A | 15% | 40% | 60% | 50% | 85% |
| B | 70% | 55% | 75% | 90% | 80% |
| C | 60% | 70% | 70% | 70% | 90% |

From the data it is apparent that the compounds tested have the effect which is characteristic of antidepressants to a more pronounced degree than TRH.

The stimulant activity of Compound B is also shown in the "wet dog shaking" test of rats (standard test listed below). The results are shown in Table IV.

Compound B was injected intraperitoneally and the animal activity is periodically observed. The effect of the substance is measured by the average number of shaking movements per minute. The dosage applied is 25 mg of substance/kilogram of body weight.

Table IV

| | WET DOG SHAKING TEST | | | | | | | | |
|---|---|---|---|---|---|---|---|---|---|
| | Minutes After Application | | | | | | | | |
| Substance | 15 | 30 | 45 | 60 | 75 | 90 | 105 | 120 | 135 |
| TRH | 2.9 | 1.0 | — | — | — | — | — | — | — |
| B | 5.25 | 3.8 | 3.2 | 2.15 | 2.1 | 1.55 | 1.05 | 0.6 | 0.3 |

From the data it is evident that Compound B is longer acting than TRH.

Other compounds of the invention showed similar results when compared to standard testing compounds such as TRH.

From this data and other work, it was found that compounds of the invention have valuable biological properties that make them useful as drugs, particularly they are useful stimulants of having long acting effect. Of marked thereapeutical importance is the effect of the compound on the central nervous system (CNS) in relationship to its endocrinological effect. In contrast to the compound TRH, the compounds of the invention show a marked shift in that relationship in favor of the valuable pharmacological properties.

The compounds of the invention are therefore useful in pharmaceutical compositions, particularly as antidepressants and stimulants. The compounds are used in therapeutically effective dosages, which may vary with the intensity or the duration of the desired effect. Preferably they are used parenterally in a dosage of 0.0 to 0.5 mg/kg orally in a dosage of 0.1 to 5 mg/kg. Depending on the desired effect, a practical range is from 0.02 parenterally in 0.2 mg/kg orally. When the therapy does not call for such dosages as stated, the dosage may be increased or decreased as recommended by the circumstances.

The substances have a surprisingly low toxicity. For instance with Substance B the following values of the $LD_{50}$ were determined:

| | Intraveneously | Intramuscularly | Orally |
|---|---|---|---|
| Rats | 1000 mg/kg | >4000 | >1000 |
| Mice | 1200 mg/kg | >4000 | >1000 |

The drugs using the compounds of the invention are prepared as is known in the prior art with inert carriers such as is known for other anti-depressants and CNS-stimulants used in human and warm-blooded animal therapy.

Reference is made to the pharmacological basis of therapeutic, Goodman and Goodman, 3rd edition, The MacMillan Company, New York (1968), especially the chapter on Drugs Used in the Treatment of Depression.

The following standard tests reported above were used.

Standard Tests

Reserpine hypothermy and
Reserpine hypomotility Test Nos. 1, 2, 3, 4, 6
Amphetamine group toxicity Test Nos. 2, 4, 5, 6
Wet shaking test of rats No. 7

(1) A. Barnett, R. I. Taber
"Antidepressant Agents"
in Screening Methods in Pharmacology
Academic Press, New York, 1971
(2) P. Simon, I. R. Boissier
Evaluating Potential Anti-Depressants in Animals
I. Int. Med. Res. 3 (Suppl. 3), 14–17 (1975)
(3) F. C. Colpaert, F. H. Lenaerts, C. I. Niemegeers, P. A. I. Janssen
A Critical Study on RO-4-1284-Antagonism in Mice
Arch. Int. Pharmacodyn. 215, 40–90 (1975)
(4) D. T. Greenwood
Animal Pharmacology of Viloxazine
I. Int. Med. Res. 3 (Suppl. 3), 18–28 (1975)
(5) I. H. Born, R. Hobbs
A Test for Tranquilizing Drugs
Arch. Int. Pharmacodyn. 63, 290–295 (1958)
(6) I. Hacke, P. Duchene-Marnelaz, G. Streinchenberger
Profil pharmacolique d'un nouvel antidepresseur non tricyclique: l'oxaflozane
Therapie 29, 81–93 (1947)
(7) E. Wei, S. Sigel, H. Lot, E. L. Way
TRH and shaking behaviour in rat
Nature 253, 739 (1975)

What we claim is:
1. The dipeptide derivative of the formula

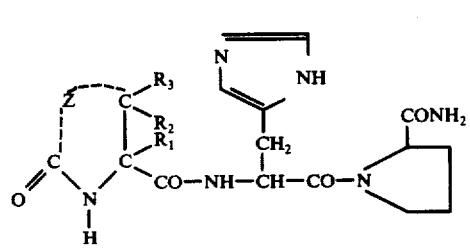

(I)

wherein $R_1$ and $R_2$ are the same or different, each one is hydrogen or alkyl having 1 to 3 carbon atoms or $R_1$ and $R_2$ considered together represent an additional bond between the carbon atoms to which $R_1$ and $R_2$ are linked;

$R_3$ is a hydrogen or alkyl of 1 to 3 carbon atoms and

Z is a divalent structure which completes the ring to a 5-or 6-membered ring, the divalent structure together with the

group to which it is attached being one of the following:

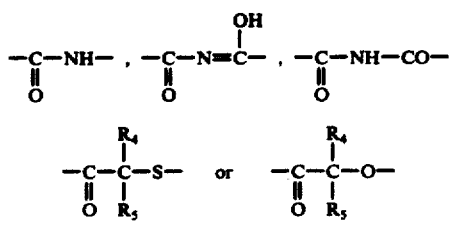

wherein $R_4$ and $R_5$ are the same or different, each one being a hydrogen or alkyl of 1 to 3 carbon atoms, hydrates thereof, and the pharmaceutically acceptable salts of these dipeptides with pharmaceutically acceptable acids.

2. The dipeptide derivative of the formula (Ia)

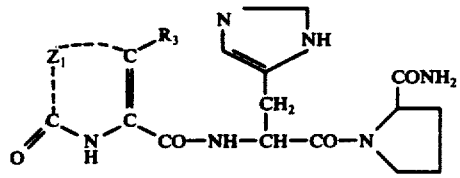

wherein $R_3$ is defined in formula I and wherein $Z_1$ together with the

group to which it is attached is a member of the group of divalent structures consisting of

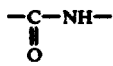

group and

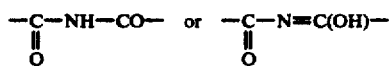

and the salts of these compounds with pharmaceutically acceptable acids.

3. The dipeptide derivative of claim 2 wherein $Z_1$ is NH—.

4. The dipeptide derivative of claim 2 wherein $Z_1$ is —NH—CO—.

5. The dipeptide of claim 1 wherein Z together with the

group to which it is attached is one of the following:

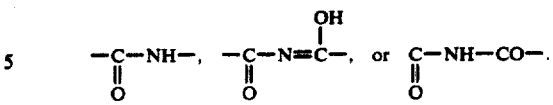

6. The dipeptide derivative of claim 2 wherein $R_1$ and $R_2$ are hydrogen.

7. The dipeptide derivative of claim 1 wherein $R_1$ and $R_2$ are alkyl of 1 through 3 carbon atoms.

8. The dipeptide derivative of claim 1 which is a 2-oxo or 5-oxo substituted imidazolidine or morpholine respectively.

9. The dipeptide derivative of claim 1 which is orotyl-histidyl-prolinamide or its pharmaceutically acceptable salt.

10. The dipeptide derivative of claim 1 which is 2-oxo-imidazolidine-4-carbonyl-histidyl-prolinamide or its pharmaceutically acceptable salt.

11. The dipeptide derivative of claim 1 which is 5-oxo-thiomorpholine-3-carbonyl-histidyl-prolinamide or its pharmaceutically acceptable salt.

12. The dipeptide derivative of claim 1 which is orotyl-L-histidyl-L-prolinamide or its pharmaceutically acceptable salt.

13. The dipeptide derivative of claim 1 which is L-2-oxo-imidazolidine-4-carbonyl-L-histidyl-L-prolinamide or its pharmaceutically acceptable salt.

14. The dipeptide derivate of claim 1 which is L-5-oxo-thiomorpholine-3-carbonyl-L-histidyl-L-prolinamide or its pharmaceutically acceptable salt.

15. The dipeptide derivative of formula I of claim 1, wherein the amino acid residues, constituting the dipeptide moieties histidine and proline, have the levo-configuration.

16. The process for the manufacture of a dipeptide derivative of formula I (I)

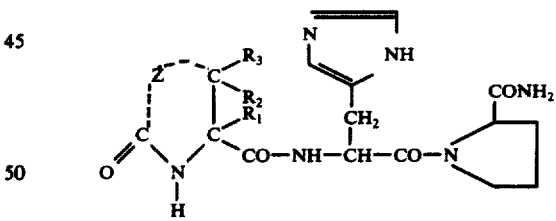

wherein $R_1$ and $R_2$ have the same or a different meaning and each represent hydrogen or an alkyl of 1 to 3 carbon atoms or together represent an additional bond between the carbon atoms to which they are bonded, $R_3$ represents a hydrogen atom or an alkyl radical containing 1 to 3 carbon atoms, and Z represents a divalent group being a member, together with the

group to which it is attached, of the group consisting of the structures

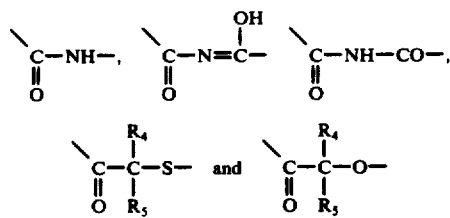

wherein $R_4$ and $R_5$ have the same or a different meaning, each one being a hydrogen or alkyl of 1 to 3 carbon atoms, hydrates thereof, and represent salts of the compounds of formula I with pharmaceutically acceptable acids, by reacting a. histidyl-prolinamide in which the 1-(3)-position of the imidazole group of the histidyl residue may be protected against acylation or a derivative thereof obtained by reacting it with a silylating agent derived from a trialkylsilanol or a dialkylsilanediol, each alkyl radical of said silylating agents containing 1 to 3 carbon atoms, with a carboxylic acid of the formulae

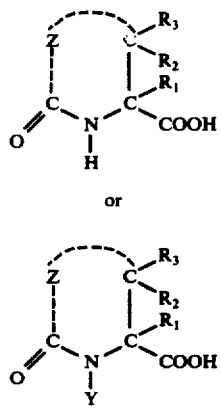

wherein $R_1$, $R_2$, $R_3$ and Z have the same meaning as above and Y represents a group cleavable by hydrogenolysis in presence of an agent, which is able to split off water or with a functional derivative selected from the following: an acid halide, anhydride, mixed anhydride, azide or an activated ester of an acid of formula II or IIa, respectively, and splitting off the group Y, the protecting group from the imidazole group contained in the histidyl residue and the silyl groups, if present, or b. prolinamide with a compound of the formula (III)

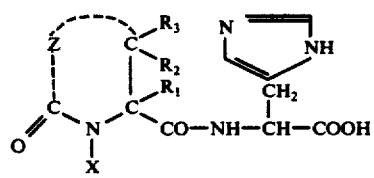

wherein $R_1$, $R_2$, $R_3$ and Z have the same meaning as above and X represents a hydrogen atom or a member of the group Y as defined before or a derivative of the compound of formula III in which the 1-(3)- position of the imidazole group is protected reversibly as described above in presence of an agent which is able to split off water, or with a functional derivative selected from the following: an acid halide, anhydride, mixed anhydride, azide or an activated ester of a compound of formula III and splitting off any protecting groups, if present, or c. a compound of formula IV (IV)

wherein $R_1$, $R_2$, $R_3$, X and Z have the same meaning as above and W represents a hydroxy, acyloxy, p-nitrophenoxy, tri- or pentachlorophenoxy-, pentafluorophenoxy, pyridyloxy, phenylmercapto, p-nitrophenylmercapto or cyanomethyloxy group or the residue of N-hydroxysuccinimide or a derivative of the compound of formula IV in which the 1-(3)- position of the imidazole group is protected reversibly as described above with ammonia or a compound generating ammonia under the reaction and splitting off any protecting groups, if present, or d. histidyl-prolinamide in which the 1-(3)-position of the imidazole group may be protected against acylation preferably by a group cleavable by hydrogenolysis with an acid of the formula (V)

wherein Hal represents a chlorine or a bromine atom in presence of an agent able to split off water with a functional derivative selected from the following: an acid halide, anhydride, mixed anhydride, azide or an activated ester of such an acid of formula V and thereafter dehalogenating the intermediate by hydrogenolysis, the removal of the protecting group - if present - being performed prior or after but preferably coincidentally with the hydrogenolysis of the halogen atom to give such compounds of formula I in which $R_1$ and $R_2$ form an additional bond between the carbon atoms to which they are bound, $R_3$ is hydrogen and Z represents —N=C(OH)— or —NH—CO—, respectively.

17. The process of section (a) of claim 16 for the manufacture of orotyl-histidyl-prolinamide which comprises reacting histidyl prolinamide with orotic acid in presence of an agent, which is able to split off water.

18. The process of claim 17 which is carried out in the presence of a carbodiimide.

19. The process of section (d) of claim 16 in which 5-chloro-or 5-bromo-orotyl-L-histidyl-L-prolinamide is subjected to a dehalogenating hydrogenolysis in presence of a noble metal catalyst to give orotyl-L-histidyl-L-prolinamide or a hydrogen halide salt thereof.

20. The process of claim 19 in which the dehalogenating hydrogenolysis occurs in presence of an agent able to bind hydrogen halides, thereby yielding orotyl-L-histidyl-L-prolinamide.

21. The pharmaceutically acceptable composition which comprises a compound of claim 1 defined in formula I in a therapeutically effective amount, and a pharmaceutically acceptable carrier.

22. The pharmaceutically acceptable composition of claim 21 wherein the compound of Formula I is L-2-oxo-imidazolidine-4-carbonyl-L-histidyl-L-prolinamide-dihydrate.

23. The pharmaceutically acceptable composition of claim 21 wherein the compound of Formula I is orotyl-L-histidyl-L-prolinamide-dihydrate.

24. The pharmaceutically acceptable composition of claim 21 wherein the compound of Formula I is L-5-oxo-thiomorpholine-3-carbonyl-L-histidyl-L-prolinamide-hydrate.

25. The composition of claim 21 wherein the therapeutically effective amount is from about 0.01 mg to 5.0 mg per kg.

26. A method of causing a psychostimulating effect, with thyrotropin releasing hormone activity on the central nervous system which comprises administering to a warm-blooded patient subject to a depressive state, a therapeutically effective amount of a composition of claim 21.

27. The method of claim 26 wherein the amount administered is from about 0.02 to 0.2 mg/kg.

28. The method of claim 27 wherein the amount administered is from 0.1 to 5 mg/kg.

29. The method of claim 26 wherein the administration is oral.

30. The method of claim 26 wherein the administration is parenteral.

31. The method of claim 26 which comprises administering the composition repeatedly and obtaining a long lasting therapeutic effect.

* * * * *